United States Patent [19]

Beyer et al.

[11] Patent Number: 4,610,631

[45] Date of Patent: Sep. 9, 1986

[54] PROCESS FOR THE PRODUCTION OF FILLINGS FOR TEETH

[75] Inventors: Hans-Hermann Beyer, Kahl; Walter Diehl, Hanau; Karlheinz Eckert, Gründau; Kurt Eiermann, Pfungstadt; Hans-Martin Ringelstein, Frankfurt am Main, all of Fed. Rep. of Germany

[73] Assignee: Degussa Aktiengesellschaft, Frankfurt, Fed. Rep. of Germany

[21] Appl. No.: 695,815

[22] Filed: Jan. 28, 1985

[30] Foreign Application Priority Data

Feb. 3, 1984 [DE] Fed. Rep. of Germany ....... 3403777

[51] Int. Cl.$^4$ .............................................. A61K 5/01
[52] U.S. Cl. .............................. 433/228.1; 433/226; 523/115; 523/116
[58] Field of Search ..................... 433/219, 226, 228.1; 106/35; 523/115, 116

[56] References Cited

U.S. PATENT DOCUMENTS 3,279,067 10/1966 Hoffman .......................... 433/226
4,064,629 12/1977 Stoner et al. ........................ 106/35

Primary Examiner—Lorenzo B. Hayes
Attorney, Agent, or Firm—Cushman, Darby & Cushman

[57] ABSTRACT

Powder of a ductile, mouth resistant metal such as silver, platinum, palladium, aluminum, or titanium, or an alloy thereof, or a cold weldable, mouth resistant synthetic resin, such as a polyacrylate or methacrylate, polycarbonate or polysulfone is worked to a paste with a plastic organic binder which liquifies at 20° to 45° C. This paste is hardened in the tooth cavity by ultrasonic action.

8 Claims, No Drawings

PROCESS FOR THE PRODUCTION OF FILLINGS FOR TEETH

BACKGROUND OF THE INVENTION

The invention is directed to a process for the production of fillings in teeth by inserting a powder into the cavity which is subsequently mechanically hardened.

A number of metallic fillers are known in preserving dentistry such as for example, amalgams, cast alloys in the form of inlays, or gold fillings. The filling of the tooth cavity with gold fillings is one of the oldest methods of filling teeth. Chemically pure gold in the form of gold foil, gold sponge, or gold powder is used for these fillings.

The gold fillings produced from pure gold are judged excellent with regard to durability, esthetics, and resistance to corrosion. However, severe disadvantages of gold fillings are the industrial and time consuming preparation of a cavity and the likewise great skill requiring depositing of the filling. Thus above all, a very careful working of the cavity with undercuts and a roughening of the cavity walls, which is not automatically feasible, are required. Both are absolute prerequisites for making the gold adhere sufficiently to the cavity. Furthermore, the cavity must be absolutely moisture free during the gold filling process. This involves not only the flow of saliva but also the breathing air of the patient. This requires the use of so-called cofferdam foils which is likewise time consuming, and occassionally very unpleasant for the patient.

Furthermore, the gold filling material must be annealed in a very clean alcohol flame immediately prior to insertion into the cavity, in order that all impurities are removed from the surface and a cohesive binding is attained between the individual gold particles. The cold weldability of gold, the foundation of the gold filling, is very greatly reduced by a contamination of the surface, especially by liquid films.

A gold filling process is known from German OS No. 3042008 in which a porous sintered body or a wire ball, made of gold, silver, platinum, iron, nickel, cobalt, aluminum, or titanium alloys is inserted into the cavity together with a plastic or liquid organic binder and by manual filling apparatuses attached to the cavity and hardened. Trouble free surfaces cannot be produced by these processes.

Therefore, it was the problem of the present invention to develop a process for the production of fillings in teeth by inserting a powdery material into the cavity and subsequently mechanically hardening it, a process which is not sensitive to moisture, permits a quick working and supplies a trouble free surface.

SUMMARY OF THE INVENTION

This problem was solved according to the invention by using a powder made of a ductile, mouth resistant metal or alloy, or made of a cold weldable mouth resistant synthetic resin which is worked to a paste with a plastic organic binder, liquifying at 20° to 45° C., and carrying out the mechanical hardening by ultrasonic action.

Preferably there is used as the binder polyethylene glycol having a molecular weight of 600 to 1500 in an amount of 0.5 to 5 weight percent. It has proven very advantageous to add about 2.6 wt. % of polyethylene glycol. The binder must be physiologically unobjectionable and advantageously should be water soluble or saliva soluble.

Above all, there have proven suitable as metal powder silver, platinum, palladium, aluminum, and titanium and their alloys, as synthetic resins polyacrylate, e.g. a cyanoacrylate polymer, polymethacrylates, e.g. polymethyl methacrylate, bisphenol A-glycidyl methacrylate polymer or methyl methacrylate-bisphenol A-glycidyl methacrylate copolymers, polycarbonates, e.g. bisphenol A-polycarbonate, polysulfone, e.g. bisphenol A-diphenylsulfone polymer, and isotactic polypropylene. Additional suitable synthetic resins are shown in Kirk-Othmer, Encyclopedia of Chemical Technology, 3rd edition, Volume 7, pages 501–508, Volume 10, pages 710–764, and Volume 11, pages 447–463. The entire disclosure of the Kirk-Othmer citations are hereby incorporated by references and relied upon as is the disclosure of German OS No. 3042008.

A paste is produced from the powder and binder and this paste is inserted in the tooth cavity in portions with a suitable tool. In the cavity it is hardened with a sonotrode under pressure and supersonic action. For example as pressing force there is needed a force of 6N at an ultrasonic frequency of 28 kilohertz.

The entire disclosure of German priority application No. P 34003777.2-41 is hereby incorporated by reference.

What is claimed is:

1. In a process for the production of a filling in a tooth by inserting a powder into the cavity and subsequently mechanically hardening same, the improvement comprising employing a powder comprising a ductile, mouth resistant metal, metal alloy or a cold weldable mouth resistance synthetic resin which has been worked into a paste with a water or saliva soluble plastic organic binder that liquifies at 20° to 45° C. and carrying out the mechanical hardening by ultrasonic action.

2. A process according to claim 1 wherein the binder comprises 0.5 to 5 wt. % of polyethylene glycol of molecular weight 600 to 1500.

3. A process according to claim 2 wherein the powder is selected from the group consisting of silver, platinum, palladium, aluminum, titanium, an alloy thereof, polyacrylate, polymethacrylate, polycarbonate, polysulfone and isotactic polypropylene.

4. A process according to claim 1 wherein the powder is selected from the group consisting of silver, platinum, palladium, aluminum, titanium, an alloy thereof, polyacrylate, polymethacrylate, polycarbonate, polysulfone and isotactic polypropylene.

5. A process according to claim 4 wherein the powder is selected from the group consisting of silver, platinum, palladium, aluminum, titanium and an alloy thereof.

6. A process according to claim 3 wherein the powder is selected from the group consisting of silver, platinum, palladium, aluminum, titanium and an alloy thereof.

7. A process according to claim 3 wherein the powder is selected from the group consisting of polyacrylate, polymethacrylate, polycarbonate, polysulfone and isotactic polypropylene.

8. A process according to claim 4 wherein the powder is selected from the group consisting of polyacrylate, polymethacrylate, polycarbonate, polysulfone and isotactic polypropylene.

* * * * *